US00PP19342P2

(12) United States Plant Patent
Lyrene

(10) Patent No.: US PP19,342 P2
(45) Date of Patent: Oct. 14, 2008

(54) SOUTHERN HIGHBUSH BLUEBERRY PLANT NAMED 'FLX-1'

(50) Latin Name: ***Vaccinium corymbosum* L.**
Varietal Denomination: FLX-1

(75) Inventor: Paul M. Lyrene, Micanopy, FL (US)

(73) Assignee: The University of Florida Board of Trustees, Gainesville, FL (US)

( * ) Notice: Subject to any disclaimer, the term of this patent is extended or adjusted under 35 U.S.C. 154(b) by 0 days.

(21) Appl. No.: 11/977,082

(22) Filed: Oct. 23, 2007

(51) Int. Cl.
*A01H 5/00* (2006.01)

(52) U.S. Cl. ..... Plt./157
(58) Field of Classification Search ..... Plt./157
See application file for complete search history.

*Primary Examiner*—Annette H Para
(74) *Attorney, Agent, or Firm*—Jondle & Associates, P.C.

(57) ABSTRACT

A southern highblush blueberry (*Vaccinium corymblosum*) cultivar particularly distinguished by having a medium-low chilling requirement (400 to 500 hours below 7° C.) producing a vigorous bush with good survival in the field, early ripening (50% ripe berries in north Florida by May 1) and berries that are large, sweet and firm.

4 Drawing Sheets

Figure 1:
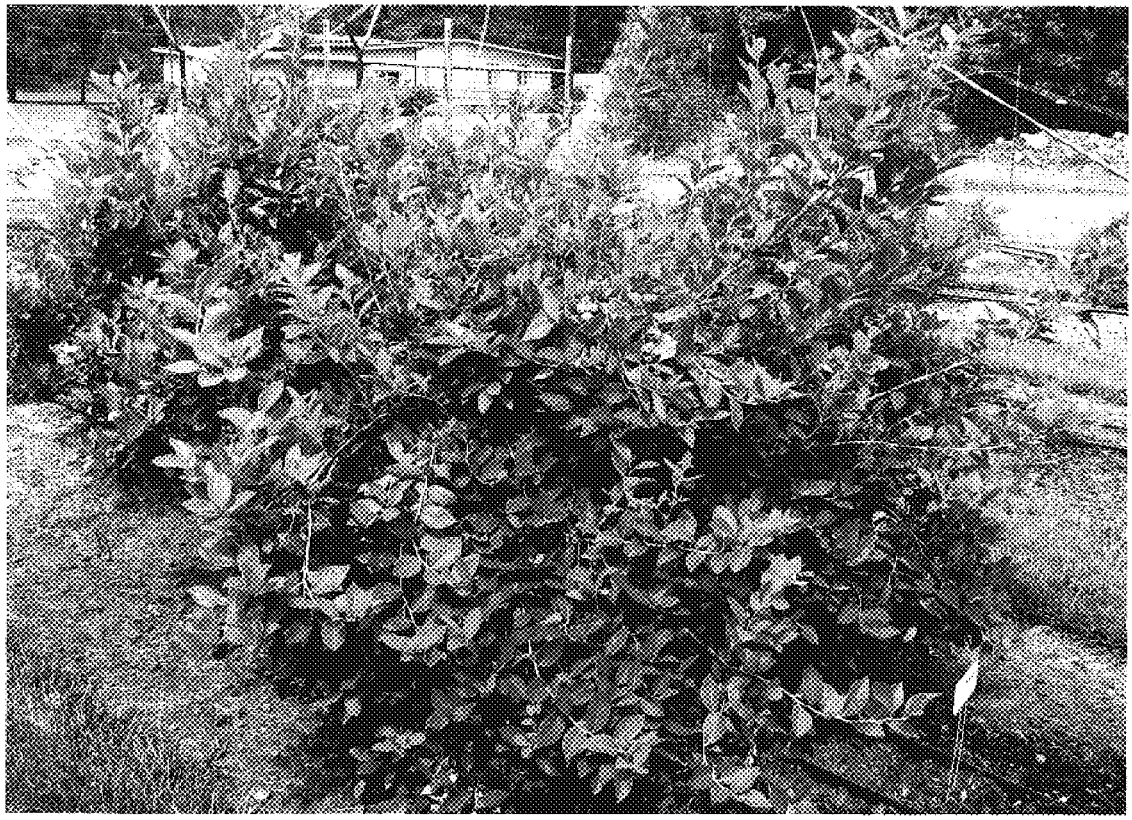

Genus and species: *Vaccinium corymbosum* L.
Variety denomination: 'FLX-1'.

BACKGROUND OF THE NEW PLANT

The invention relates to a new and distinct variety of southern highbush blueberry (*Vaccinium corymbosum* L.) hybrid plant named 'FLX-1.' 'FLX-1' is a southern highbush blueberry clone distinguished by its low chilling requirement, its vigorous, upright bush and by its very firm sweet berries that ripen from late April through mid-May when grown in north Florida and during may around Bakersfield, Calif. Several hundred plants of 'FLX-1' have been propagated by softwood cuttings at Gainesville, Fla., and the resulting plants have all been phenotypically indistinguishable from the original plant.

'FLX-1' originated as a seedling from the cross of the proprietary female parent, 'FL 92-103' (unpatented) with the male parent, 'FL 90-163' (unpatented) which was made as part of the University of Florida breeding program in a greenhouse at Gainesville, Fla. in March, 1992. The seedling was first fruited in a high-density field nursery in the spring of 1994. After the third year of fruiting in the field, in the spring of 1996, 'FLX-1' was propagated by softwood cuttings in June, 1996, and a 20-plant test plot was established as part of a variety test in a commercial field at Windsor, Fla. in January, 1997. Because of the vigorous, upright bush and high berry quality, 'FLX-1' was re-propagated by softwood cuttings in the summer of 1999, and 190 test plots were planted in a second test plot at the same farm in March 2003. A test planting of rooted cuttings was established in western Oregon and in the San Joaquin Valley of California in 2002. These plots were observed carefully from flowering through fruit ripening each year, and no mutations of off-type plants have been observed. The present invention has been found to retain its distinctive characteristics through successive asexual propagations.

SUMMARY OF THE INVENTION

The following are the most outstanding and distinguishing characteristics of this new cultivar when grown under normal horticultural practices in Florida.

1. A medium-low chilling requirement;
2. A highly vigorous, upright bush;
3. Early ripening (50% ripe berries in north Florida by May 1); and
4. Berries that are large, sweet and firm.

DESCRIPTION OF THE PHOTOGRAPHS

The color chart used in this specification is "The Pantone Book of Color", by Leatrice Eiseman and Lawrence Herbert. (1990). Harry N. Abrams, Inc., Publishers, N.Y. Where colors in the drawings differ from the Pantone color designations in the descriptions, the Pantone color designations are accurate. The colors shown are as true as can be reasonably obtained by conventional photographic procedures.

FIG. 1 shows a row of 'FLX-1' plants in a test block in western Oregon. The high vigor and bright-green leaves are visible. In north Florida, the plant has been more upright in growth than those pictured.

Figure 2:
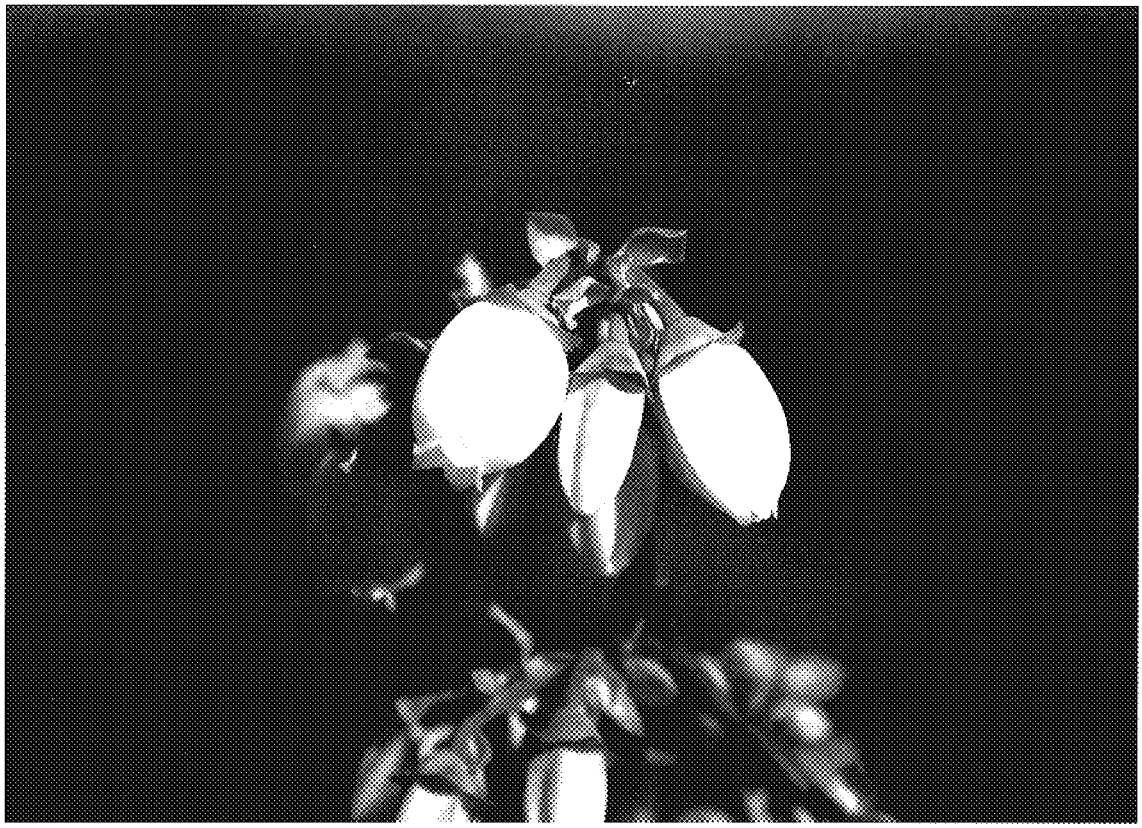

FIG. 2 shows the flowers of 'FLX-1'. In color, the flowers have deeper shades of pink before they open. Cold weather during flowering intensifies the pink pigments.

Figure 3:
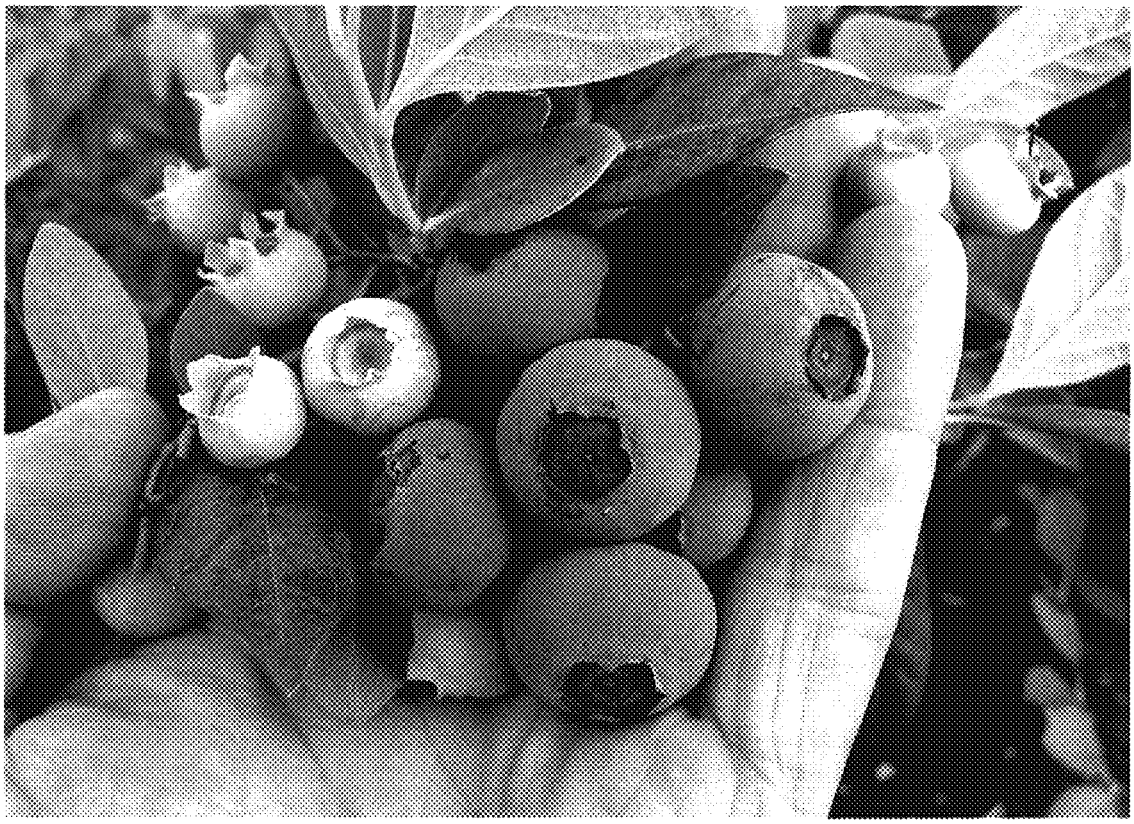

FIG. 3 shows clusters containing mature and immature berries on a field-grown plant. The large berries and the flattened calyx of the mature fruit are shown.

Figure 4:
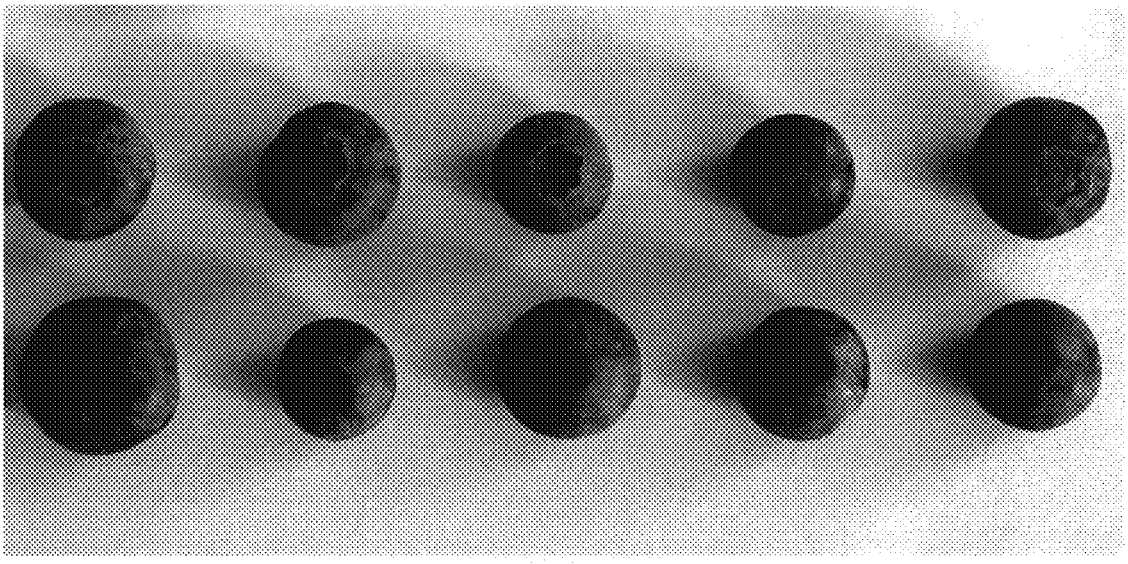

FIG. 4 shows berries at close range. The small, dry picking scar and rather flat calyx are visible. The color of the berries is darker than FIG. 3 because some of the surface wax was removed in handling the berries to arrange them for photography.

DESCRIPTION OF THE NEW CULTIVAR

The following detailed description sets forth the distinctive characteristics of 'FLX-1'. The data which define these characteristics were collected from asexual reproductions carried out in Florida. The plant history was taken on 7-and one-half year-old plants. The following descriptions relate to plants grown in the field in north Florida (Windsor, Fla.). Color designations are from "The Pantone Book of Color"

(by Leatrice Eiseman and Lawrence Herbert; Harry N. Abrams, Inc., Publishers, New York, 1990). Where the Pantone color designations differ from the colors in the Drawings, the Pantone colors are accurate.

DETAILED BOTANICAL DESCRIPTION

Classification:

*Family: Ericaceae.*

*Botanical.*—*Vaccinium corymbosum* L.

*Common name.*—Southern Highbush Blueberry.

Parentage:

*Female parent.*—'FL 92-103', a proprietary southern highbush blueberry plant (unpatented).

*Male parent.*—'FL 90-163' a proprietary southern highblush blueberry plant (unpatented).

Market Class: 'FLX-1' produces southern highbush blueberries suitable for both the fresh and processed fruit markets.

Plant:

*General.*—Bush characteristics were taken from a plot of twenty 7.5 years-old plants growing in a test plot in a commercial field near Windsor in northeast Florida.

*Plant height.*—2.5 m.

*Canopy* (*diameter measured at widest part of the bush*).—1.8 m.

*Plant vigor.*—High; more vigorous and faster growing than 'Star'.

*Growth habit.*—Upright.

*Flower bud density* (*number*) *along flowering twigs in January.*—Medium.

*Twigginess.*—Low.

*Tendency toward evergreenness.*—Medium.

*Productivity.*—In northeast Florida, 'FLX-1' produces at least 5 pounds of berries per bush on plants 3 years old or older.

*Chilling requirement.*—400 to 500 hours below 7° C.

*Cold hardiness.*—Flowers and fruit are hardy to −3° C., the plant is hardy to −15° C. during winter dormancy.

*Ease of propagation.*—'FLX-1' is easy to propagate from softwood cuttings; the plants survive and grow well in nursery beds.

Trunk and Branches:

*Suckering tendency.*—Medium; seven-year-old plants have an average of 15 major canes rising from a crown 30 cm in diameter.

*Surface texture* (*of strong, 6-month-old shoots observed in August*).—Smooth.

*Surface texture* (*of strong, 1-year-old wood observed in August*).—Becoming rough with vertical cracks.

*Surface texture* (*of 3-year-old and older wood*).—Rough due to fine-textured pattern of vertical cracks.

*Color of 6-month-old twigs observed in August in the field.*—"Celery Green", Pantone 13-0532.

*Color of 1-year-old, rough bark observed in August.*—"Celery Green", Pantone 13-0532 becoming "Copper Brown", Pantone 18-1336.

*Color of 3-year-old rough-textured canes.*—"Birch", Pantone 13-0905.

*Internode length on strong, upright shoots measured in August.*—1.4 cm.

Leaves:

*Length, mean* (*including petiole, from tip of petiole to end of blade*).—7.5 cm.

*Width, mean* (*at widest point*).—3.5 cm.

*Shape.*—Ovate, terminating in a very short dew tip, 0.03 cm long.

*Margin.*—Minutely serrate; with sessile glands along the margin of petiolar half of the leaf blades; these glands are visible at 30X magnification; otherwise entire.

*Color.*—Upper surface: "Chive", Pantone 19-0323. Lower surface: "Mistletoe", Pantone 16-0222.

*Pubescence on upper surface of leaves.*—Scattered, curled, short white hairs on the midrib, otherwise glabrous.

*Pubescence on the lower surface of leaves.*—Absent.

*Pubescence on margins.*—Absent.

*Relative time of leafing versus flowering.*—In commercial fields in North Florida, normally flower a week or more before new leaves begin to appear; full leafing is often delayed for several additional weeks on plants grown in Florida.

Flowers:

*Arrangement.*—Flowers are arranged alternately along a short, leafless, deciduous branch.

*Fragrance.*—Little or none.

*Shape.*—Urceolate.

*Flowering period.*—Mean date of 50% open flowers in Windsor, Fla. is February 17; averages 10 days before 'Star'.

*Cluster* (*tight, medium, loose*).—Loose.

*Average number of flowers per cluster.*—5.

*Pedicel.*—Length at time of anthesis: 0.4 cm. Color: "Periodot", Pantone 17-0336.

*Peduncle.*—Length at time of anthesis: Highly variable; median is 0.6 cm. Color: "Periodot", Pantone 17-0336.

*Calyx.*—Cup diameter at anthesis 9 tip of lobe to tip of opposite lobe): 0.5 cm; calyx lobes are unusually short for a southern highbush blueberry cultivar. Surface texture: Smooth. Color at anthesis: "Peridot", Pantone 17-0336.

*Corolla.*—Length of tube: 0.9 cm. Diameter of tube (at widest point): 0.6 cm to 0.7 cm. Aperture diameter: 0.3 cm. Surface texture: Smooth. Color at anthesis: "Parchment"; Pantone 13-0908. Length (from pedicel attachment point to corolla tip excluding the pedicel): 1.1 cm to 1.2 cm.

Reproductive Organs:

*Style length* (*top of ovary to stigma tip*).—0.8 cm.

*Location of tip of stigma relative to lip of the corolla.*—Stigma tip is about 0.1 cm inside of the end of the corolla tube; if the style were 0.1 cm longer, the stigma tip would extend just to the outer edge of the corolla tube.

*Pistil color at anthesis.*—"Herbal Green", Pantone 15-0336.

*Pollen.*—General: The pollen includes some tetrads in which one or two spores have aborted. Although pollen staining appears to be slightly below normal, pollen fertility is not expected to be a problem in commercial fields. Abundance of shed: High. Staining with 2% acetocarmine (a measure of potential pollen fertility): 95%. Color of dried pollen: "Yolk Yellow", Pantone 14-0846.

Self Fruitfulness: Very low; only two berries matured from 100 flowers hand self-pollinated in the greenhouse.

Fruit:

*Mean date of first commercial harvest* (*25% of berries ripe*).—April 20.

*Mean date of mid-harvest.*—May 1.

*Mean date of last harvest.*—May 20.

*Diameter of calyx aperture on mature berry.*—0.7 cm.

*Size and shape of calyx lobes on mature berry.*—Calyx lobes flat against berry surface making a fairly well-defined star shape on most berries.

*Depth of calyx dish.*—0.1 cm.

*Pedicel length on ripe berry.*—0.5 cm.

*Peduncle length on ripe berry.*—Highly variable; medians is 1.0 cm.

*Detachment force for ripe berries.*—Medium to low.

Number of berries per cluster.—4.

Berry:

*Cluster* (*tight, medium, or loose*).—Medium to loose.

*Weight* (*on well-pruned plants*).—2.4 g per berry compared to 1.8 g per berry for 'Star'.

*Height.*—1.47 cm.

*Width.*—1.73 cm.

*Shape.*—Subglobose; equatorial diameter slightly greater than polar diameter.

*Surface color of mature berries while on the plant.*—"Blue Fox", Pantone 14-4804.

*Surface color of the berries after harvesting and packing.*—"Purple Cloud", Pantone 16-3919.

*Surface color of ripe berry after polishing.*—"Shale", Pantone 19-4019.

*Internal flesh color of ripe berry.*—"Leek Green", Pantone 15-0628.

*Surface wax.*—Medium in amount and in persistence during handling of the berry.

*Pedicel scar.*—Small and dry.

*Firmness.*—High.

*Flavor.*—Sweet, subacid.

*Texture.*—Good; small seeds, juicy and thin skinned.

Seeds:

*Color of dried seeds.*—"Tobacco Brown", Pantone 17-1327.

*Weight of well-developed dried seed.*—0.57 mg per seed.

*Length of well-developed dried seed.*—0.17 cm.

*Width of well-developed dried seed.*—0.09 cm.

Resistance to Diseases, Insects and Mites: 'FLX-1' has grown vigorously but does not survive well in the field in north Florida; the short plant life is believed to be due to susceptibility to stem blight, caused by the fungus *Botryosphaeria dothidia,* which is widespread and endemic in the southeastern United States; in trials in areas with warm but dry summers, 'FLX-1' has not shown problems with stem blight; in north Florida, 'FLX-1' has shown average to above-average resistance to fungal leaf spots.

COMPARISON WITH PARENTAL AND KNOWN CULTIVARS

'FLX-1' differs from the proprietary female (seed) parent 'FL 92-103' (unpatented) in that 'FLX-1' has a larger, firmer berry and a more upright growth habit than 'FL 92-103'.

'FLX-1' differs from the male (pollen) parent 'FL 90-163' (unpatented) in that 'FLX-1' has a larger berry than 'FL 90-163'. Additionally, 'FLX-1' has an excellent picking scar while 'FL 90-163' has a poor picking scar.

'FLX-1' differs from the commercial variety 'Star' (U.S. Plant Pat. No. 10,675), an important variety widely planted in Florida and Georgia for early-season blueberry production. 'FLX-1' is more vigorous and upright with a higher yield potential than 'Star'.

I claim:

1. A new and distinct cultivar of southern highbush blueberry plant as shown and described herein.

* * * * *